United States Patent [19]
Schlameus et al.

[11] Patent Number: 5,294,446
[45] Date of Patent: Mar. 15, 1994

[54] COMPOSITION AND METHOD OF PROMOTING HARD TISSUE HEALING

[75] Inventors: Herman W. Schlameus; William C. Fox; Donald J. Mangold, all of San Antonio; Robert G. Triplett, Dallas; George R. Holt, San Antonio; Thomas B. Aufdemorte, Lakeway, all of Tex.

[73] Assignee: Southwest Research Institute, San Antonio, Tex.

[21] Appl. No.: 815,997

[22] Filed: Jan. 2, 1992

Related U.S. Application Data

[63] Continuation-in-part of Ser. No. 389,455, Aug. 7, 1989, abandoned.

[51] Int. Cl.⁵ ............................................. A61K 9/14
[52] U.S. Cl. ...................... 424/489; 424/484; 424/485; 424/488; 424/490; 424/493; 424/93 R; 424/93 U; 435/178; 435/182; 514/21; 604/890.1
[58] Field of Search ............... 424/484, 485, 483, 488, 424/490-499, 93 B, 93 R, 93 U; 435/178, 179, 182; 514/21; 530/399; 604/890.1; 623/16, 66

[56] References Cited

U.S. PATENT DOCUMENTS

| 4,391,909 | 7/1983 | Lim | 435/178 |
| 4,609,551 | 9/1986 | Caplan | 424/93 |
| 4,642,120 | 2/1987 | Nero | 623/16 |
| 4,647,536 | 3/1987 | Mosbach | 435/177 |
| 4,663,286 | 5/1987 | Tsang | 435/178 |
| 4,673,566 | 6/1987 | Goosen | 424/19 |
| 4,798,786 | 1/1989 | Tice | 435/177 |
| 5,053,050 | 10/1991 | Itay | 623/16 |
| 5,158,934 | 10/1992 | Ammann | 514/900 |

Primary Examiner—Thurman K. Page
Assistant Examiner—G. S. Kishore
Attorney, Agent, or Firm—Benjamin Adler

[57] ABSTRACT

Osteoprogenitor cells encapsulated in alginate and alternatively, additionally encapsulated in poly-L-lysine and/or agarose promote regeneration of bone at the site of implantation. The present invention provides a composition comprising osteoprogenitor cells embedded or encapsulated in alginate and the use of said microcapsules for the facilitation of bone regeneration.

9 Claims, 5 Drawing Sheets

LIVE CELLS
ALGIN MATRIX

LIVE CELLS
POLYLYSINE-ALGIN MEMBRANE
LIQUID MEDIUM

LIVE CELLS
ALGIN MATRIX
BIODEGRADATION-RESISTANT MATERIAL

COMPOSITION AND METHOD OF PROMOTING HARD TISSUE HEALING

CROSS-REFERENCE TO RELATED APPLICATION

This application is a continuation-in-part of application Ser. No. 07/389,455, filed Aug. 7, 1989, entitled "Composition and Method of Promoting Hard Tissue Healing" now abandoned.

FIELD OF THE INVENTION

The present invention relates generally to the field of hard tissue healing and, more particularly, to the field of biodegradable implantable microcapsules to stimulate the natural process of hard tissue regeneration and bone wound healing.

BACKGROUND OF THE INVENTION

Defects in bone or osseous structures will initiate the process of bone healing. Healing often involves the replacement of injured tissue by connective tissue and leaves a scar. Bone, under optimal conditions, heals by regeneration in which injured tissues are replaced by their own kind and leaves no scar. The success of regeneration following injury depends, among other things, on the type of injury, the adequacy of treatment and the systemic health of the patient. Osseous repair involves at least six physiological stages: impact, induction, inflammation, soft callus formation, hard callus formation, remodeling and regeneration. Heppenstall, *Fracture Treatment and Healing*, W. B. Saunders, Philadelphia, 1980, page 35.

With inadequate treatment, severe injury and/or metabolic bone disease, fracture healing is significantly retarded. For example, in the case of a metabolic bone disease such as osteoporosis, 40% of patients with decreased bone mass due to osteoporosis showed a markedly impaired fracture repair rate. Only 33% of women in whom significant osteoporosis was present were able to achieve a solid union following femoral neck fractures. In comparison, a successful union was achieved in 90% of women having a physiologically normal bone mass a successful union was achieved. Lane et al., Osteoporosis, Orthopedics Clinics North America 15: 711 (1984); Arnold, *J. Bone Joint Surg.* 66A: 847 (1984); Scileppe et al., *Surg. Form* 32: 543 (1981).

Approximately 200,000 hip fractures in osteoporotic women occur in the United States annually. The women have a 40% mortality rate due to complications of repair of these fractures. As a result, there is a significant need to facilitate fracture repair in these types of patients. In addition, fractures in young accident and trauma victims result in loss of numerous productive days from the work place. For example, it takes an average of six weeks to repair even simple bone injuries in healthy individuals.

Bone fractures and bone wound healing following trauma or surgery account for considerable morbidity and mortality. For example, femoral neck fractures in patients under forty may be associated with avascular necrosis in as many as 40% of cases complicated by non-union. Kyle et al., *Young Femoral Neck Fractures*, (Abst.), Annual Meeting of American Academy of Orthopedic Surgery, Atlanta, Ga. (1984). Many other examples could be cited of the need for more expeditions methods to facilitate and/or accelerate repair of fracture or hard tissue defects.

Since the feasibility of the preparation of artificial cells was first demonstrated in 1957 by Chang (Chang, T. M. S. (1964) Science:146, 524), numerous approaches to their production and use have been evaluated. Artificial cell membranes have been reported using a variety of synthetic and biological materials to give the desired membrane properties. A large variety of materials can be enclosed (microencapsulated) in artificial cells. These include single and multienzyme systems, cell extracts, and combined enzyme-adsorbent systems (Chang, U.S. Pat. No. 4,642,120). One disadvantage of this prior art is based on the fact that these previous patents were based on the encapsulations of biological cells to prevent them from being adversely affected by external factors and immunological rejection (Chang, Biomedical Applications of Immobilized Enzymes and Proteins (Plenum: New York, 1977) Vols. 1 and 2; Mosbach et al. (1966) Acta Chem. Scan. 20: 2807; Lim et al. (1980) Science 210: 908). More recently, the microencapsulation of living biological cells that can be maintained in culture has been disclosed (Lim et al. (1980) Science 210: 908; U.S. Pat. No. 4,391,909). Unfortunately, the intent of past studies on the microencapsulation of living cells has focused on protecting these cells for storage. These previous studies on microencapsulated cells did not recognize the use of microencapsulation to facilitate the healing process.

Thus, there is a great need in the area of orthopedic medicine for compositions and methods of using microencapsulated living cells that will facilitate bone and heart tissue regeneration.

SUMMARY OF THE INVENTION

In order to facilitate the healing of bone and other hard tissue fractures and defects and facilitate structural implant fixation, a microcapsule has been developed. Specifically, a system of biocompatible encapsulating materials has been discovered in which osteoprogenitor cells can be embedded in or encapsulated while retaining their viability and biological function. Additionally, this osteoprogenitor cell encapsulating material will degrade at a rate proportional to the material process of bone healing, while releasing viable cells without prompting a deleterious histologic response. Finally, this biomaterial and autologous tissue device will promote healing of nonhealing bone defects by providing osteoprogenitor cells, tissue (proteins or fats) and a scaffolding tissue guiding during the appropriate phase of the bone healing process.

The biocompatible encapsulating materials useful in practicing this invention can have different rates of biodegradeability. The biocompatible material may be readily biodegradable, slowly biodegradable or relatively resistant to degradation in biological fluids. A readily biodegradable material is one that is degraded 50% or more within hours to several days by contact with biological fluids. A slowly biodegradable material will degrade at least 50% when in contact with biological fluids for more than several days up to several weeks. A material resistant to biodegradation is one which retains its integrity for at least several months in the presence of biological fluids. The inclusion of a material resistant to biodegradation provides a structure scaffolding for guiding bond tissue regeneration.

Materials which are readily biodegradable (bioerodable) include naturally-occurring polymers such as alginates, poly-L-lysine, cellulose polymers, (e.g., methylcellulose, collagen, gellen gum, casein, chitosan, and the like. Materials which are slowly degradable include some polyesters, and polyanhydrides.) Biocompatible materials which are relatively resistant to biodegradation include titanium oxide, hydroxyapatite, biocompatible metal compositions, biocompatible ceramic compositions, and the like. The microcapsules of the present invention can comprise one biodegradable material or a combination of two or more biodegradable materials. In the latter case, the microcapsule may contain biocompatible materials of varying rates of biodegradability. This system of biodegradable material allows the timed release of cells as well as other tissue involved in promoting bone healing. Combining multiple materials having different release rates allows the microcapsule to mimic the hosts's biologic response to bone injury.

These and other objects, as well as the nature, scope, advantages and utilization of this invention, will become readily apparent to those skilled in the art from the following description, the drawings and the appended claims.

DETAILED DESCRIPTION OF THE INVENTION

Figure 1:
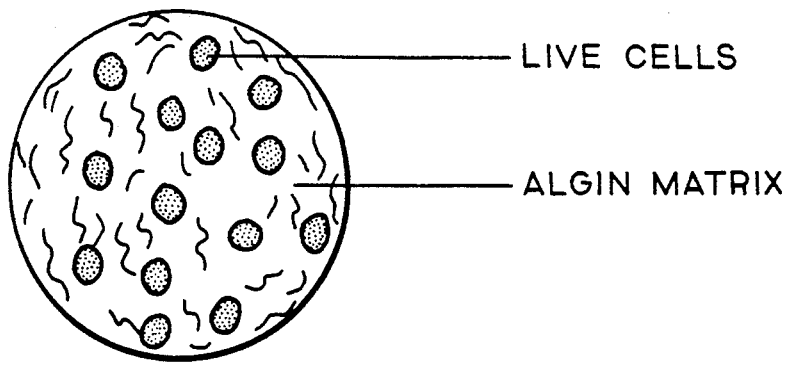
FIG. 1 shows a schematic of three capsule types. One containing cells embedded in a single biodegradable polymer, a second with cells in a two polymer system, and a third encapsulation containing cells and a material resistant to biodegradation.
Figure 1:
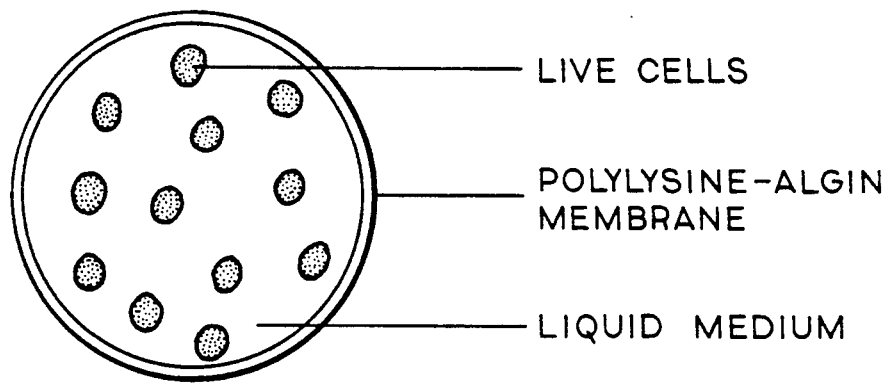
Figure 1:
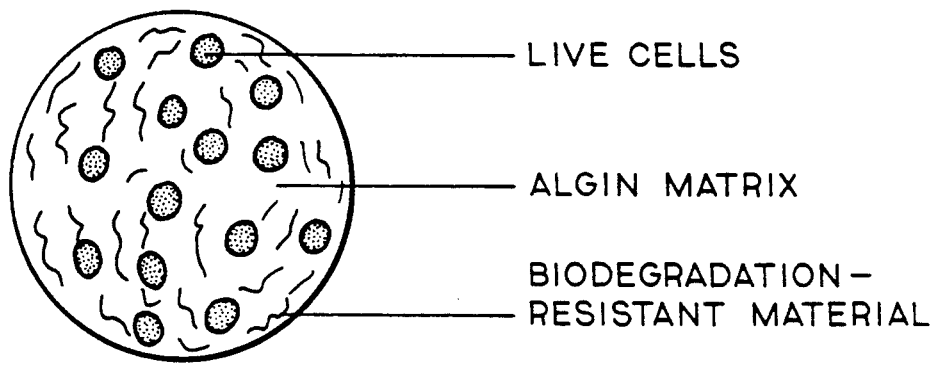

In order to accomplish the above objects and objectives, the present invention provides, in one embodiment, osteoprogenitor cells embedded or encapsulated in an alginate matrix.

In one embodiment of the present invention, osteoprogenitor cells have been encapsulated, viability maintained within artificial membranes, and the cells when implanted in an animal model, subsequently proliferate and maintain their capacity to induce osteogenesis.

The osteoprogenitor cells useful in carrying out the present invention can be any cells capable of inducing the formation of regenerated bone. Preferably, these cells are autologous bone progenitor cells harvested from the individual in need of such treatment. These cells may be harvested from the site of the injury or from a distant site for transplantation to the injury site. The primary cells may be used directly or may be modified in cell culture. In another embodiment coincident with the administration of antirejection drugs, such as cyclosporine, the osteoprogenitor cells may be harvested from another individual of the same species as the individual to be treated. In selecting the osteoprogenitor cells for use in the present invention it is important to try to minimize the rejection of the implanted cells for the period necessary to induce the regeneration of new bone.

The preferred composition of the present invention comprises osteoprogenitor cells embedded or encapsulated in a biodegradable material. The cells may either be embedded in a matrix material by being dispersed within the matrix material itself or by surrounding the cells with a biodegradable material. In either case, in order to decrease the rate of release of the osteoprogenitor cells from the microcapsule, the cells may be further encapsulated in a slowly biodegradable material which has a prolonged integrity in the host such as poly-L-lysine. Preferably, the matrix material is an alginate, such as sodium alginate. The matrix material may also be selected from the group consisting of gellan gum, chitosan, or agarose. Materials resistant to biodegradation are included to provide a scaffolding material for bone to grow up to and through.

The method of encapsulating the osteoprogenitor cells comprises embedding or encapsulating the cells in a biodegradable material by any of the techniques known to those of skill in the art. Preferably, the osteoprogenitor cells are encapsulated by a modification of the method disclosed in U.S. Pat. No. 4,391,909, incorporated herein by reference. Briefly, osteoprogenitor cells were gently dispersed in a solution of sterile sodium alginate and pumped through a needle into a collection bath of 1.3% calcium chloride containing Tween 20. The alginate embedded cells, also termed herein microcapsules, were harvested, washed with saline and either used directly for implantation or injection into the treatment site or further encapsulated to prolong the integrity in the host.

In a preferred embodiment, the microcapsules were formed into wafers to facilitate implantation. These wafers were preferably composed of agar, such a wafer is described in Example 4. The wafer can be of any material that is biocompatible and can be formed into a hydrogel having characteristics similar to agar such that the handling and placement of the microcapsules at the treatment site is facilitated.

The method of treating bone fractures of the present invention comprises the implantation of the osteoprogenitor microcapsules of the present invention into a fracture site of an individual and allowing sufficient time for the formation of new bone at the treatment site. The osteoprogenitor microcapsules may be implanted by surgical procedures known to those of skill in the art or may be injected into the fracture site utilizing a suitable pharmaceutical carrier. The choice of such carriers will be obvious to those in the art.

A microcapsule comprising one or more biodegradable materials can itself be coated or further encapsulated by a less readily degradable substance in order to further delay complete release of the encapsulated material. By carefully choosing the materials used as the initial encapsulating material and the subsequent coating or encapsulating material, one of skill in the art may control the rate of release of one or several encapsulated materials, including the encapsulated osteoprogenitor cells. For instance, in one embodiment, alginate alone can be used as the sole encapsulating material. In a second embodiment, biodegradability is retarded by coating thus-prepared alginate microcapsules with a polyanionic polymer such as poly-L-lysine.

In yet another embodiment, a core material relatively resistant to biodegradation, such as a ceramic material, is initially bound to and later slowly releases a second material, one of the above-mentioned growth factors. A second material may be released from a portion of the surface of the core material. The bound core material is encapsulated within a more readily biodegradable material. The encapsulated material may itself contain the same or other treating materials, e.g., the same or another growth factor, antiviral agents, or hormones. For instance, a microcapsule comprising woven titanium mesh mixed with collagen may be also be embedded within the alginate microcapsule containing osteoprogenitor cells. Prosthetic devices formed of the present invention will facilitate fixation of orthopedic devices or dental implants by enhancing the bone regeneration at the site of prosthetic implantation. In another example, fixation of orthopedic implants at the surgical site can be facilitated by implantation of the composition of the present invention comprising ceramic hydroxyapatite adsorbed with bone derived growth factor (or any other material which stimulates the differentiation or growth of osteoprogenitor or cartilage progenitor cells) with the progenitor cells in the encapsulating materials. This embodiment allows a stable and solid support for replacement and/or reconstruction of defective hard tissues while additionally providing the necessary progenitor cells to repair and/or replace the defective hard tissue structures.

As indicated above, microcapsules prepared in accordance with this invention can additionally contain materials which aid in bone healing or in the prevention or treatment of complications of trauma. Such additional materials can include, but are not limited to, extracellular matrix of chondrocytes (ECM), hormones, growth factors such as somatomedins, fibroblast growth factor, bone morphogenic protein, platelet derived growth factor, bone inductive growth factor, osteoinductive growth factor, cartilage derived growth factor, prostaglandins, macrophage derived growth factors, bone derived growth factor, skeletal derived growth factor, epidermal growth factor, transforming growth factor, growth factor, cytokines, and the like, or a combination of any of these. Such materials are alternatively termed herein hard tissue promoting factors. A second group of agents which aid in treatment or prevention of the complications of trauma may be included. Examples of this second group of agents are, without limitation, antiviral, anti-inflammatory, analgesic, or antibacterial agents and similar preventative agents. The above preventative agents and tissue promoting factors may be used alone or in combination in practicing the present invention. Such materials can be prepared by any method known to those skilled in the art, including purification from naturally occurring sources and recombinant technology.

The microcapsules of this invention, coated, e.g., with poly-L-lysine, or uncoated, can be further surrounded by a material that can be formed into a hydrogel wafer (such as agar, gelatin, gellan gum or the like) to facilitate handling and transfer or implantation of encapsulated material(s) into the site of treatment.

The present invention provides compositions and a method to facilitate the healing or regeneration of bone, for instance, at fracture sites. This method comprises implantation or injection of any of the compositions of the present invention into a site or a device in an individual at which bone fixation, reconstruction, regeneration or healing is desired. The osteoprogenitor cells then proliferate and cause the deposition of new bone material at the implantation or injection site.

The term "individual" is meant to include any animal, preferably a mammal, and most preferably a human, cat, dog, or horse.

Artificial cell preparation was carried out in a sterile environment. All equipment, materials, solutions, etc. were either sterilized by the appropriate means or purchased as sterile before use in the process.

Having now generally described the invention, a more complete understanding can be obtained by reference to the following specific examples. These examples are provided for purposes of illustration only and are not intended to be limiting unless otherwise specified.

EXAMPLE 1

Procedure for Encapsulation of Osteoprogenitor Cells

A. Preparation of osteoprogenitor cells.

Cells were isolated from canine trabecular bone specimens. The specimens represented material obtained by biopsy of the iliac crest of four research grade mongrel dogs numbered as follows: 4452, 4386, 4593, and 4467. The biopsy specimens from each dog were processed individually in order to permit autologous implantation of the cellular material at a later date, thereby circumventing any possible rejection response and eliminating the need for immune suppression of the host dogs.

The biopsy material was washed multiple times in Dulbecco's modified Eagle's medium (DMEM) containing penicillin (1000 units/ml), streptomycin (1000 ug/ml), and amphotericin-B (0.25 ug/ml) to remove adherent tissue and debris. The bony trabeculae were then cut into small pieces (1–2 mm$^2$) followed by a second series of washings to remove hematogenous elements. The resulting clean pieces of bone were placed in a 100 mm cell culture dish in the absence of media and incubated at 37° C. in an atmosphere of $O_2$/$CO_2$ (95/5 v/v). After 20 minutes, 10 ml DMEM containing 10% newborn calf serum (NCS) was carefully added to the dish without disturbing the bone fragments. The dishes were returned to the incubator and left undisturbed for 5 days. Subsequently, the media was changed every three days to fresh DMEM with 10% NCS. After 23 days of culture, the cells which had migrated from the bone fragments onto the surface of the culture dish were removed with trypsin/EDTA (0.125%/1 mM).

These migrated cells were placed in a T-75 culture flask and designated first passage cells. The cells were passaged two more times to yield third passage cells which, when confluent, were encapsulated as described below (Runs 1-30A through 1-31B). Examination of aliquots of the encapsulated cells suspended in DMEM containing the vital dye trypan blue, indicated that the cells had retained their viability during the encapsulation procedure. The encapsulated cells were maintained in DMEM containing 10% NCS at 37° C. in an atmosphere of $O_2/CO_2$ (95/5 v/v) for 24–48 hours prior to preparation for implantation into nonunion sites prepared in the radii of dogs. Viability experiments revealed that the encapsulated cells could be maintained in this manner for three days without a decrease in cell number. In fact, the cell number increased by 70-90% during this time period.

Cells for implantation in nonunion fracture sites in dogs were harvested and grown in culture as described above. Osteoprogenitor cells were incubated in an incubator (37° C.) until ready for use in the encapsulation process.

B. Encapsulation of Cells

Three types of encapsulated cells were prepared. In one, cells were encapsulated (or embedded) in an algin matrix. In the second, the process was carried further and the alginate embedded cells were further encapsulated using poly-L-lysine/alginate as the capsule membrane. In a third, alginate embedded cells were further embedded with materials resistant to biodegration. A schematic of the three capsule types is shown in FIG. 1.

The encapsulated cells were prepared as follows and used for implantation into animals to demonstrate the effect on fracture healing. Cells from several flasks were combined, placed in a 15-ml sterile culture tube and rinsed 3 times with sterile 0.9% saline solution. After decanting the saline solution from culture tube, 10 ml of sterile sodium alginate solution (about 1%) was added. The alginate used for most of the cell encapsulation was sterile Macrocarrier solution obtained from Bellco Glass, Inc. The cells were gently dispersed and the cell/alginate solution was transferred to a sterile syringe. The syringe was placed in a sterile pump device and connected to the encapsulation device with sterile tubing.

A sterile collection bath (containing a 1.3% calcium chloride solution with 0.25 ml of 10% Tween 20) was placed under the encapsulation device. The cells were encapsulated in the alginate and collected in the collection bath. After the alginate encapsulated cells remained in the collection bath for 3-5 minutes, they were passed through fine wire screen baskets. The alginate embedded (encapsulated) cells were then rinsed 2 times with 0.9% saline solution and used in this form as the alginate matrix cell preparation.

In some situations when it is desirable to provide poly-L-lysine encapsulated osteoprogenitor cells, the alginate embedded (encapsulated) cells were rinsed once with a poly-L-lysine solution, preferably about 0.2%. The poly-L-lysine used in the encapsulation was obtained from Sigma Chemical Company and had a molecular weight of approximately 38,000. The cells were then incubated in the poly-L-lysine solution for 5-7 minutes, rinsed 2 times with 0.9% saline solution, and finally, rinsed once with an approximately 1.5% sodium citrate solution by incubating the encapsulated cells in the sodium citrate solution for 5-7 minutes. The cells were then rinsed 2 times with 0.9% saline solution and 3 times with DME (Dulbecco's Modified Eagle's Medium) for 2-3 minutes. The cells suspended in approximately 40 ml DME were transferred to a sterile T-75 flask and incubated at 37° C. until implantation.

Figure 2:
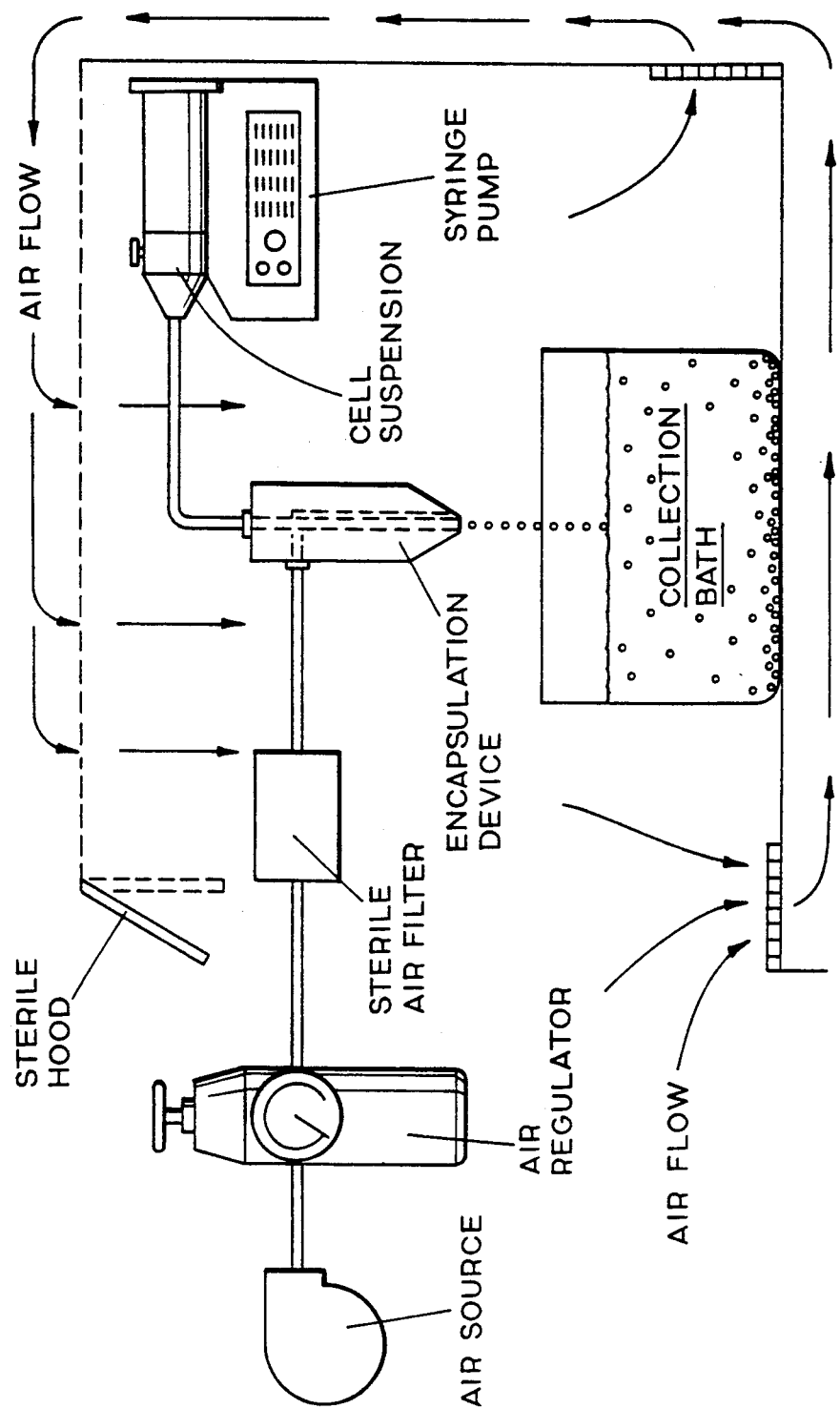
FIG. 2 shows a schematic of the type of apparatus used to form one type of microcapsule.

The results of the encapsulation procedures are shown on Table 1. In the initial runs (1-1A through 1-9D) only placebo capsules were prepared in order to adjust process parameters to produce the desired type of capsule. Matrix materials evaluated during this period included alginates, casein, chondroitin sulfate, and collagen. In the preferred embodiment, spheres were formed using sodium alginate collected in a calcium chloride (CaCl2) bath as shown in Run 1-7A in Table 1. In forming the capsule, air regulation was used to control the droplet size. A schematic of the apparatus used is shown in FIG. 2.

Runs following 1-12A were carried out with encapsulating live cells unless otherwise stated. The encapsulation of osteoprogenitor cells are designated as 1-30A through 1-31B in Table 1.

TABLE 1

PREPARATION OF ENCAPSULATION OSTEOPROGENITOR CELLS AND/OR GROWTH FACTORS[a,b]

| Date | Run No. | Cell Type | Coating Treatment | Size Range (μ) | Comments |
|---|---|---|---|---|---|
| 5/19/88 | 1-2 | Placebo | — | 900–1000 | Capsules produced for stability study. Pump fed. |
| 5/23/88 | 1-3 | " | — | 500–850 | Decreased capsule size by reducing needle diameter (18 gage to 20 gage). |
| 8/25/88 | 1-4A | " | — | 700–1000 | Capsules produced for stability study (in blood plasma). |
|  | 1-4B | " | 3300 Poly-l-lysine 0.05% in M-Q-HOH | " | " |
|  | 1-4C | " | 6000 Poly-l-lysine 0.05% in M-Q-HOH | " | " |
|  | 1-4D | " | 38,500 Poly-l-lysine 0.05% in M-Q-HOH | " | " |
| 8/29/88 | 1-5A | " | 3300 Poly-l-lysine 0.1% in M-Q-HOH | " | " |
|  | 1-5B | " | 3300 Poly-l-lysine 0.2% in M-Q-HOH | " | " |
|  | 1-5C | " | 6000 Poly-l-lysine 0.1% in M-Q-HOH | " | " |
|  | 1-5D | " | 6000 Poly-l-lysine 0.2% in M-Q-HOH | " | " |
|  | 1-5E | " | 38,500 in Poly-l-lysine 0.1% in M-Q-HOH | " | " |
|  | 1-5F | " | 38,500 in Poly-l-lysine 0.2% in M-Q-HOH | " | " |
|  | 1-5G | " | — | " | " |
| 11/15/88 | 1-7A | " | — | " | Placebos to be used for implantation. |
|  | 1-7B | " | 6000 Poly-l-lysine 0.2% in M-Q-HOH | " | " |
| 12/1/88 | 1-9 | UTHSC-609 & 713 | — | " | No encapsulation problems. |
| 12/8/88 | 1-12 | UTHSC-609 & 713 | — | 700–1000 | Encapsulation device fed by hand. Bone growth factor added to sample matrix. |
| 12/15/88 | 1-14 | " | — | " | Encapsulation device fed by hand. Bone growth factor added to sample matrix. |
| 12/19/88 | 1-15 | " | — | " | Encapsulation device fed by hand. Bone growth factor |

TABLE 1-continued
PREPARATION OF ENCAPSULATION OSTEOPROGENITOR CELLS AND/OR GROWTH FACTORS[a,b]

| Date | Run No. | Cell Type | Coating Treatment | Size Range ($\mu$) | Comments |
|---|---|---|---|---|---|
| 12/29/88 | 1-16 | " | — | " | added to sample matrix. Encapsulation device fed by hand. Bone growth factor added to sample matrix. |
| 1/5/89 | 1-17 | " | — | " | Encapsulation device fed by hand. Bone growth factor added to sample matrix. |
| 1/12/89 | 1-18 | " | — | " | Encapsulation device fed by hand. Bone growth factor added to sample matrix. |
| 1/23/89 | 1-19 | UTHSC-609 | — | " | No cells available from Subject 713. No bone growth factor added. |
| 2/16/89 | 1-20 | UTHSC-609 & 713 | 8000 Poly-l-lysine 0.2% in M-Q-HOH | " | All cells were tritium labeled. No bone growth factor added. |
| 2/23/89 | 1-21 | " | 8000 Poly-l-lysine 0.2% in M-Q-HOH | " | Encapsulation device fed by hand. Bone growth factor added to sample matrix. |
| 3/2/89 | 1-22 | " | 8000 Poly-l-lysine 0.2% in M-Q-HOH | " | No bone growth factor added. |
| 3/9/89 | 1-23 | " | 8000 Poly-l-lysine 0.2% in M-Q-HOH | " | Bone growth factor added. Trypsinization procedure failed to yield bone cells from Subject 713 resulting in substitution of placebos for cells. |
| 3/16/89 | 1-24 | " | 8000 Poly-l-lysine 0.2% in M-Q-HOH | " | Encapsulation device fed by hand. Bone growth factor added to sample matrix. |
| 3/24/89 | 1-25 | " | 8000 Poly-l-lysine 0.2% in M-Q-HOH | " | Encapsulation device fed by hand. Bone growth factor added to sample matrix. |
| 10/25/89 | 1-28 | UTHSC-609 & 713 | — | " | All cells were tritium labeled. Trypsinization procedure was carried out by UTHSC. Bone growth factor added to sample matrix. |
| 11/29/89 | 1-29 | " | — | " | Encapsulation device fed by hand. Bone growth factor added to sample matrix. |

[a]Capsule Matrix - Sterile sodium alginate from Bellco Biotech.
[b]Collection System - Calcium chloride - 1.3% with 13 mM Hepes.

Histopathologic analysis was performed on encapsulated cells maintained in vitro as well as on tissues removed at necropsy from animals implanted with microencapsulated osteoprogenitor cells for in vivo evaluation. This was accomplished in three phases as described in Examples 2, 3, and 4, below.

EXAMPLE 2

In Vitro Cell Analysis

Following encapsulation of the cells, in vitro studies were conducted to determine osteoprogenitor cell viability and define their morphology within artificial cell membranes. Histologic sections were prepared and stained with hematoxylin and eosin using encapsulated cells in the following combinations:

K-1 Alginate+U2OS cells (an osteosarcoma cell line)
K-2 Poly-L-lysine+U2OS cells
K-3 Alginate+normal dog cells (animal #4452)
K-4 Poly-L-lysine+normal dog cells (animal #4452)
K-5 Alginate+FL cell tumor (a transformed human tumor cell line capable of bone formation)

U2OS cells encapsulated in alginate appeared as small nests or colonies numbering approximately 2-15 cells, each with an average of approximately 10 cells per group. The cells had basophilic staining nuclei which were round and regular with prominent nucleoli noted at random. Cell cytoplasm was moderately eosinophilic and cell boundaries were relatively distinct. The alginate matrix was amorphous and slightly basophilic but obviously degrading as a consequence of the histologic processing procedure necessary to produce the sections.

U2OS cells encapsulated in poly-L-lysine also appeared as clusters with morphology not significantly different from that described above, however, the artificial poly-L-lysine membranes were histologically distinct as slightly basophilic undulating cuticular surfaces enclosing cell nests. The undulation was interpreted as an artifact of dehydration, again necessary for processing.

When encapsulated in alginate, normal dog cells appeared as isolated groups, usually of 2-3 cells. Morphologically the cells had the characteristics of osteoblasts with eccentrically located round nuclei and relatively conspicuous eosinophilic cytoplasm. In some cells there was evidence of a perinuclear eosinophilic condensation typical of osteoblasts. Again, the alginate membranes appeared to be degrading as a result of the histological preparation.

Normal osteoprogenitor dog cells encapsulated in poly-L-lysine showed similar morphology to those encapsulated in alginate alone. Again, poly-L-lysine membranes were distinct as described with the U2OS cells above.

Alginate embedded FL cells also showed isolated cells or groups of 2-4 cells with round, eccentrically located nuclei, occasional prominent nucleoli and eosinophilic cytoplasm. The FL cells differed from U2OS cell lines in that FL cell clusters were in general smaller and less numerous within the artificial membranes.

In summary, all artificial cell preparations contained viable cells with morphology varying as to the derivation of the particular cell type indicating that no deleterious effects resulted from the encapsulation process.

Alginate cell membranes degraded during histological processing and thus were not visible in subsequent sections produced from animal studies. Poly-L-lysine membranes were more distinct and durable and remained visible at least in early phases of the animal studies. The interpretation of the in vivo data shown in the Examples below was made in accordance with these observations.

These studies demonstrate that cells may be encapsulated, their viability maintained, and sections prepared for histologic analysis. Intact cells were noted within the confines of the artificial membranes and, as a consequence, these formulations rendered viable cells for implantation studies.

EXAMPLE 3

In Vivo Studies of Encapsulated Cell Lines Implanted in Nude Mice

Cell viability following encapsulation was evaluated in vivo using FL cells, a transformed line of human amnion cells capable of tumor formation in the nude mouse. The rationale for these experiments follows. Since the alginate is rapidly dissolved in vivo, cells encapsulated in alginate and implanted beneath the skin of the nude mouse formed tumors as rapidly as nonencapsulated cells injected subcutaneously. Formation of tumors by cells encapsulated in poly-L-lysine was delayed because poly-L-lysine is not readily dissolved in the host and cells first have to multiply within the capsules in sufficient mass to burst them.

Encapsulated FL cells (Runs 1-15B, 1-16B, 1-36A, and 1-36B) were maintained overnight at 37° C. in an atmosphere of $O_2/CO_2$ (95/5 v/v). The following morning 0.5 ml alginate or poly-L-lysine encapsulated cells were surgically implanted beneath the skin of 3-week old nude mice of the nu/nu strain (Harlan). The mice were sacrificed at 16 and 32 days after implantation for gross and histological evaluation of tumor formation.

FL cell lines encapsulated in alginate and implanted for a period of 16 days, demonstrated at necropsy, viable cells with histologic features remarkably similar to those described in the in vitro experiments with the exceptions that the cell clusters were now much larger, often forming confluent nests in excess of several hundred cells.

Alginate membranes, as expected, were not visible due to degradation of the membranes, but the general outlines of the artificial cells were present in some areas, perhaps attributable to fibrocollagenous connective tissue proliferating in proximity with the artificial cell membranes. Where the membranes existed, FL cells had grown into confluent nests with the subcutaneous tissue and muscles, violating and disrupting the boundaries of the artificial cell membranes. In these areas of host-FL cell tumor interface, conspicuous bone and osteoid production was noted.

FL cells encapsulated in poly-L-lysine and implanted for 16 days again showed large viable cell clusters with morphologic features as described above with the exception that the cell membranes of poly-L-lysine remained intact. Most cell groups within the membranes had grown to confluency. No evidence of cell penetration into adjacent tissues, as was noted above, was apparent. No bone or osteoid production was visible.

FL cell lines encapsulated in alginate/poly-L-lysine harvested 32 days after implantation showed a large bulk of tumor (larger than 2.0×1.0 cm) with FL cell line morphology. It was composed of confluent nests and sheets of cells proliferating in no discernable pattern. Most membrane material apparently had been resorbed and was inconspicuous. There was overt invasion of host tissue by the FL cell lines with conspicuous bone and osteoid production.

Thus, the above results have demonstrated the viability of encapsulated osteoprogenitor cells and further that this viability could be maintained throughout the implantation or injection procedure with the encapsulated cells subsequently proliferating within artificial membranes, rupturing the membranes and invading into host tissues.

Additionally, the above results demonstrate that cell lines induced bone production and evidence of the maintenance of cell capacity to exhibit their normal function following the encapsulation process. Alginate and poly-L-lysine microcapsules apparently degrade at different rates, as evidenced by discernable differences between poly-L-lysine and alginate encapsulated cells were noted at 16 days with alginate tending to degrade earlier than poly-L-lysine.

In order to determine if artificially encapsulated cells would survive in vivo, 7 nude mice were injected with encapsulated cells formulated in varying matrices. Vital cells encapsulated in poly-L-lysine and alginate membranes could be observed 24 days following injection.

EXAMPLE 4

In vivo Studies of Treatment of Fracture Non-unions Produced in Dogs

Fracture nonunions were experimentally induced in 11 research grade dogs. The nonunions were performed by surgically removing a 3 mm disc of cortical and cancellous bone from the mid-radius. Dogs were then allowed to resume normal weight bearing activities and, after 12 weeks, stable fracture nonunions were produced. The dogs were then divided into groups consisting of controls receiving only matrix material with no osteoprogenitor cells and four animals receiving osteoprogenitor cells formatted in varying ways. Each dog received cells which had been harvested at the time of the initial surgery and maintained in tissue culture as described in Example 1 above.

In order to facilitate handling during the implantation procedures and to insure retention at the nonunion site, the encapsulated cells were prepared in a gel of low melt agarose (Sigma TYPE VII). A "doughnut" prepared with 3 ml of 4% agarose was formed in a 28 mm diameter culture dish with a 12 mm diameter post in the center. After the agarose had gelled, the centerpost was removed. A suspension was prepared from 3 ml encapsulated cells and 3 ml 2% agarose. The hole in the center of the 4% agarose doughnut was filled with 1.5 ml of this suspension. After the central portion had gelled, the entire doughnut was transferred to a cell culture dish, covered with DMEM, and returned to the incubator. The doughnuts were implanted into the nonunion defects within 15-18 hours. The outer rim of the doughnut was substantial enough to permit gentle handling with forceps. The central core was rigid enough to hold the encapsulated cells at the implant site, while still allowing for diffusion of wound and tissue fluid to the cells. These doughnuts were then implanted following excision of the fibrous nonunion material and the radii splinted with a 4-hole stainless steel splint. The dogs then resumed weight bearing activity for an additional 12 weeks at which time the animal was sacrificed and material taken for detailed histologic evaluation.

The two dogs receiving only poly-L-lysine matrix material showed a persistent nonunion defect occupying approximately 8.5-11% of the original nonunion defect volume on histomorphometric analysis. The trabecular bone volume in these areas was calculated at 6.5 and 24.75% respectively with 46.9 and 18.9% fibrous connective tissue intermixed as well as a small amount of fibrocartilage. In addition, a significant quantity of poly-L-lysine matrix, visible as irregularly shaped refractile material, was noted throughout the defect. There was a modest multinucleate foreign body giant cell response to this material as well as minimal chronic inflammatory cell infiltration. The histologic features from the two control dog studies were identical to six control dogs from previous studies involving the encapsulation and implantation of bone inductive proteins in nonunion fractures.

When autologous osteoprogenitor cells were encapsulated in an artificial matrix of alginate and implanted in a dog nonunion, histologic examination showed a dramatic and complete healing of the fracture nonunion. This was apparent on histomorphometric analysis with 100% of the original defect being filled with new bone. The trabecular bone volume in this area was 55% with no interposed fibrous connective tissue. Relatively normal cancellous space was present instead. This was in dramatic contrast to the controls and other test animals receiving inductive proteins. Also apparent were isolated small cell clusters and groups of cells with round, elliptically located nuclei and relatively distinct cytoplasmic membranes with slight eosinophilia to the cytoplasm. These were identical to cell clusters noted in the in vitro and nude mouse in vivo experiments. These cells could be observed within the cancellous space and at times in intimate adaptation with an acellular eosinophilic homogeneous material consistent with osteoid.

When autologous osteoprogenitor cells were encapsulated in a poly-L-lysine matrix and implanted in a dog nonunion, histologic examination 3 weeks demonstrated evidence of degrading artificial cell membranes consistent with poly-L-lysine and a few artificial cell nests as described above in the in vitro and in vivo nude mouse studies, as well as the dogs previously described. Throughout the nonunion site there was evidence of brisk osteoblastic activity with production of homogeneous, eosinophilic acellular osteoid as noted in the previous dogs. The histologic features demonstrated healing at a significantly advanced stage compared with that anticipated for control animals from previous nonunion experiments. The two remaining dogs each received poly-L-lysine encapsulated cells or alginate encapsulated cells. Both dogs were carried to 13 weeks. The poly-L-lysine cells showed some evidence of osteoid production and remnants of artificial cells, but no significant fill of the nonunion defect. The same was true of the last dog receiving alginate encapsulated cells.

The results of the implantation of osteoprogenitor cells encapsulated in alginate (with or without poly-L-lysine) demonstrated that the method of the present invention causes complete healing of the fibrous nonunion, the healed fracture being composed of mature bone with lamellar characteristics and evidence that remodeling of the fracture site into a functional state had occurred.

The above examples conclusively demonstrate that osteoprogenitor cells may be encapsulated in artificial membranes, their viability maintained, and these cells subsequently implanted in living subjects (mice and dogs). The cells subsequently proliferate out of the artificial confines to produce osteoid and new bone which contributes to the healing process.

Although all dogs receiving encapsulated osteoprogenitor cells did not demonstrate the same amount of nonunion fracture healing, this result may relate to a number of complex interrelated factors. These include the kinetics of artificial cell membrane degradation, cell release from artificial membranes, proliferative capabilities of individual autologous cells, differences inherent in healing capacity of each animal, or combinations of these.

In addition, bone inductive factors may be necessary in the artificial membranes to completely signal encapsulated cell populations to begin proliferation within the unfavorable environment of a healing wound. Some of these variables may be overcome by inclusion of bone cell differentiation factors within the microcapsule at the time of encapsulation.

EXAMPLE 5

Evaluation of Encapsulated Cells and Bone Inductive Growth Factors

The extent of microencapsulation degradation in vivo was determined by histologic review of analytical bone implant (ABI) system acquired osseous tissue samples. Poly-L-lysine and sodium alginate microencapsulated osteoprogenitor cells and bone inductive growth factors were placed in baboon tibia using the ABI and sampled following various hearing intervals. To perform the in vivo experiments, each of two baboons was implanted with six ABIs. ABIs were implanted in the medial aspects of the proximal, central and distal tibia of each leg. Five different microencapsulation implant system formulations were tested in each of the two baboons.

Five forty-two day experiments were initiated. Each experiment involved: (1) culturing of autologous bone to obtain osteoprogenitor cells, (2) preparation of the microencapsulation system, (3) implantation of loaded microencapsulations, (4) culturing of the naive microencapsulated materials, (5) histologic review of the naive loaded microencapsulations, (6) healing, (7) retrieval of osseous tissue and implant materials, and (8) histologic preparation and review of the in vivo specimens removed from the ABI.

Osseous tissue was surgically removed from the two baboons during the implantation of the ABIs. This tissue was used to provide autologous tissue for cell culture and subsequent encapsulation. Osteoprogenitor cells were readily cultured and were harvested following second passage.

During implantation of the microencapsulation systems, standard operating procedures for the ABI surgical protocol were utilized. Following exposure of the ABI, 0.9 grams plus or minus 0.1 grams were placed in five of the six ABI sites. The sixth site served as a control site for the subjective comparison of histologic differences in healing. Following surgical closure, all animals were returned to their cages and normal care. Both baboons were implanted in each of five sites with one of the five microencapsulation systems. Following implantation, one site in each baboon was sampled at every seven days. Each microencapsulation system had two samples acquired following 7, 14, 21, 28 and 35 days. On the 42nd day, the sixth or control site was sampled. This 42 day healing sample from the sixth ABI site was used to verify that osseous healing was proceeding in a normal fashion during the course of the 42 day experiment. This 42 day experimental protocol was utilized for each of the five microencapsulation systems. Following the performance of one 42 day experiment the two baboons enrolled on the project were allowed to recover from the experimental procedures for periods ranging from 30–90 days.

The ABI tissue samples were fixed and formalin, embedded, and sections were prepared to determine the histologic response to those microencapsulations and measure the quantity of microencapsulated materials. The amount of microencapsulating material found was termed residual microencapsulation. Three grading levels were assigned to those microencapsules. Grading levels zero meant that there were no microencapsulated materials (either fragments or whole capsules) left in the tissue. Grading level 1 meant that there were occasional intact microcapsules but the majority of the material left consisted of microencapsulation fragments. Grading level 2 meant that there were intact microcapsules in the tissues.

Figure 3:
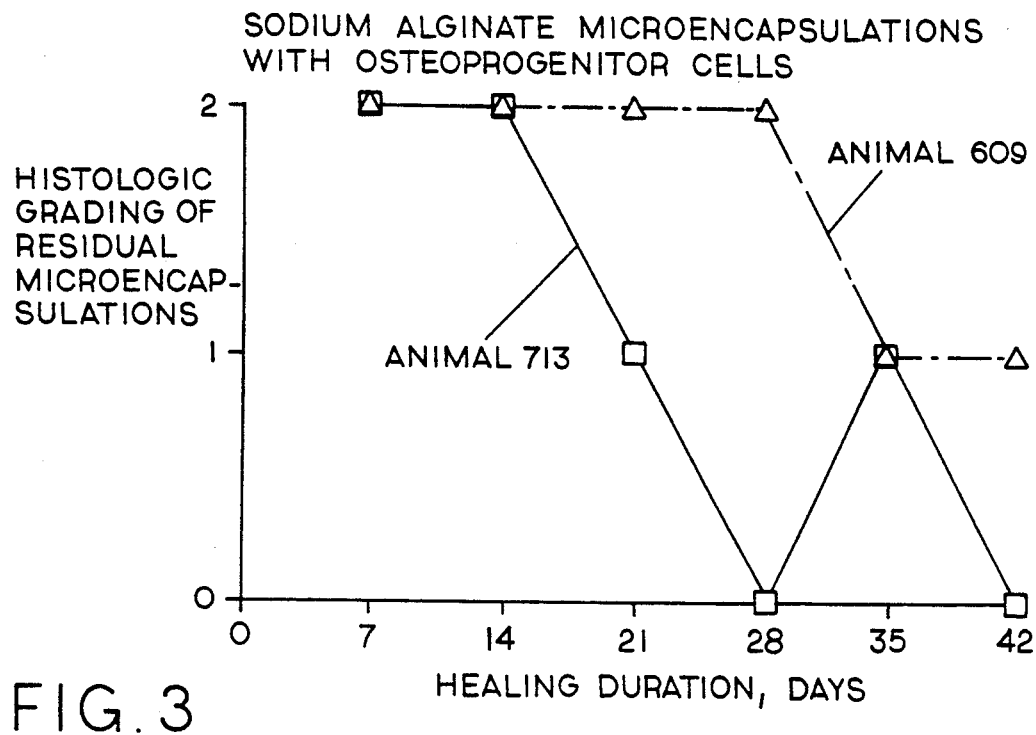
FIG. 3 depicts the histologic interpretation of residual microencapsulations from osteoprogenitor cells microencapsulated with sodium alginate.
Figure 4:
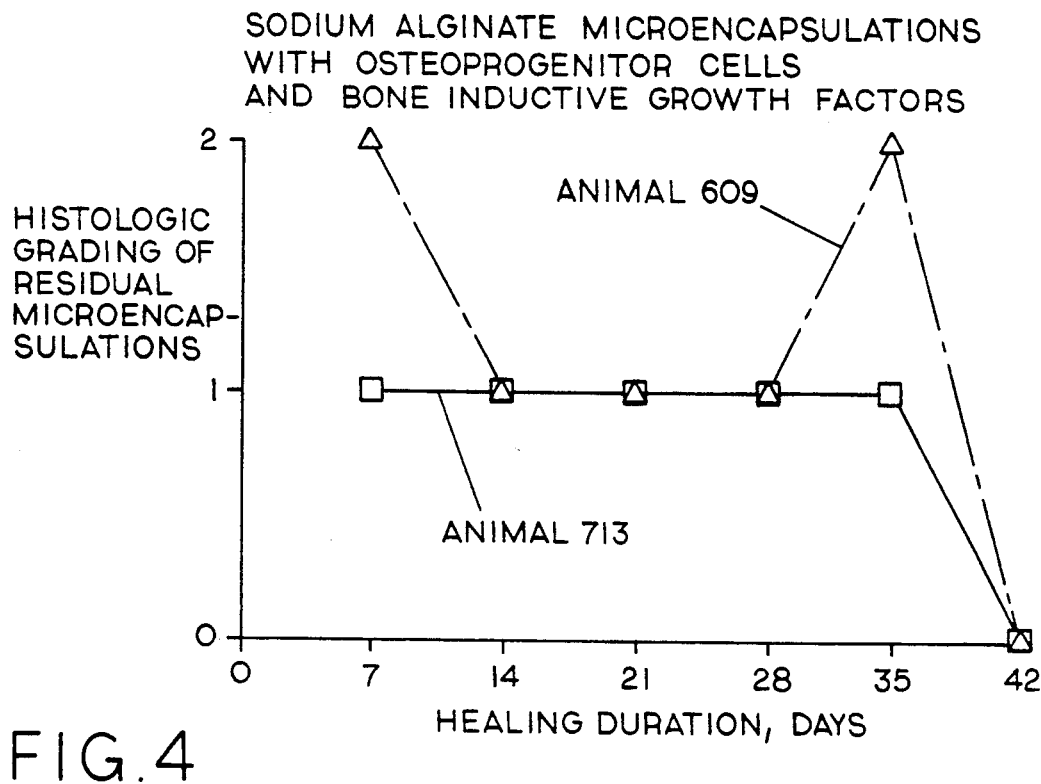
FIG. 4 depicts the histologic interpretation of residual microencapsulations in sodium alginate microencapsulation containing osteoprogenitor cells and bone inductive growth factors.
Figure 5:
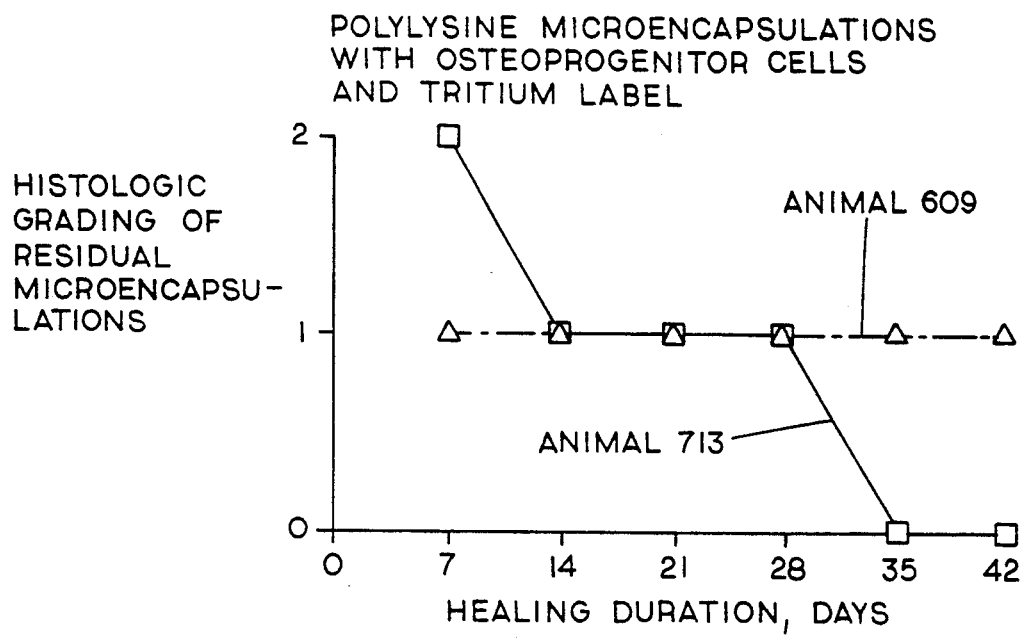
FIG. 5 depicts the histologic interpretation of residual microencapsulations in poly-L-lysine microencapsulations of osteoprogenitor cells and a tritium label.
Figure 6:
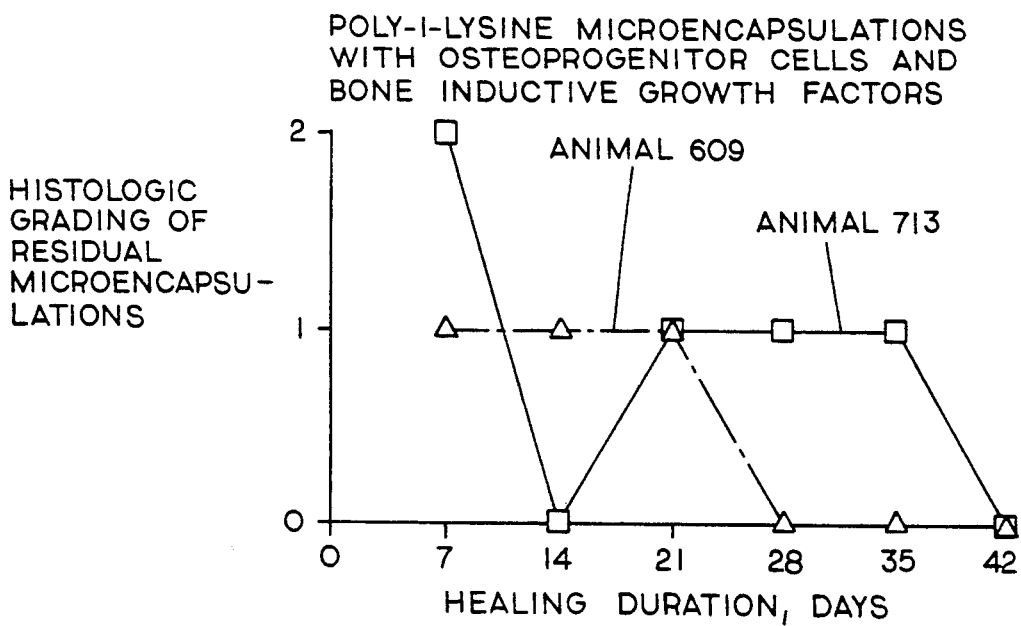
FIG. 6 shows the histologic interpretation of residual microencapsulations from poly-L-lysine microencapsulations of osteoprogenitor cells and bone inductive growth factors.
Figure 7:
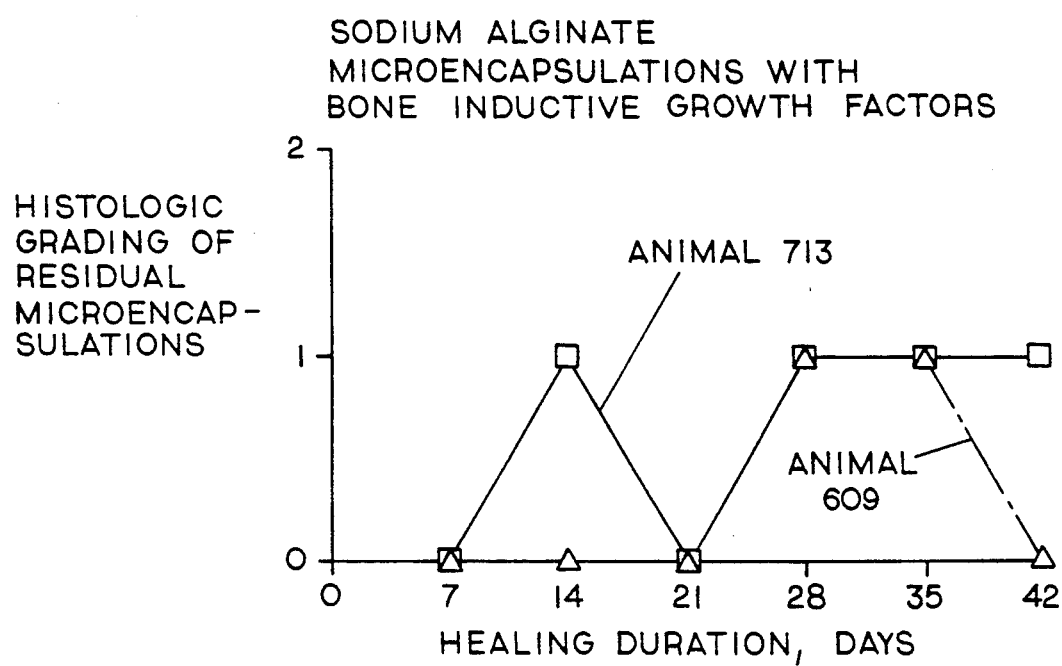
FIG. 7 shows the histologic interpretation of residual microencapsulations of sodium alginate microencapsulations containing bone inductive growth factors.

The first release rate experiment involved sodium alginate microencapsulation containing osteoprogenitor cells (FIG. 3). The second release rate experiment involved sodium alginate microencapsulation containing osteoprogenitor cells and bone inductive growth factors (FIG. 4). The third release rate experiment involved poly-L-lysine microencapsulation containing osteoprogenitor cells with a tritium label (FIG. 5). The fourth release rate experiment involved poly-L-lysine microencapsulation containing osteoprogenitor cells and bone inductive growth factors (FIG. 6). The fifth release rate experiment involved sodium alginate microencapsulation containing bone inductive derived growth factors (FIG. 7).

Abscess formation was not present in these experiments. Chronic inflammation was infrequent and there was little evidence of fibrosis or foreign body giant cell response. With multiple re-entries into surgical sites, and the addition of osteoprogenitor cells on bone inductive growth factors, abscess formation, fibrosis, acute and chronic inflammation and focal foreign body giant cells responses were seen. In spite of these reactive changes, bone formation did occur. Microencapsules were degraded and some intact capsules showed persistent viable osteoprogenitor cells.

In the sodium alginate microencapsulations with bone inductive growth factors, no intact microcapsules were seen at any time point. Thus, even by seven days, only fragments were visible.

The results presented show three significant bone healing changes. (1) Encapsulated osteoprogenitor cell or bone inductive factors slowed the promotion of vigorous bone formation spontaneously healing wound. (2) Osteoprogenitor cells survival within the encapsulants was demonstrated at all points in bone healing when microencapsulations were present and intact. (3) Capsule degradation proceeded faster in the alginate system that in the poly-L-lysine system and both systems degraded in a slightly longer physiologic time frame.

The invention now being fully described, it will be apparent to one of ordinary skill in the art that many changes and modifications can be made thereto without departing from the spirit or scope of the invention as set forth below.

What is claimed as new and is desired to be covered under letters patent is:

1. A composition of matter useful in facilitating osseous healing comprising osteoprogenitor cells and a bone inductive growth factor encapsulated in a biocompatible microcapsule made from a biodegradable polymer selected from the group consisting of alginate, poly-L-lysine and alginate coated with poly-L-lysine.

2. The composition of claim 1, wherein said bone inductive growth factors are selected from the group consisting of somatomedins, fibroblast growth factor, bone morphogenic protein, platelet derived growth factor, osteoinductive growth factor, cartilage derived growth factor, prostaglandins, macrophage derived growth factors, bone derived growth factor, skeletal derived growth factor, epidermal growth factor, transforming growth factor, growth factor and cytokines.

3. The composition of claim 1 further comprising a material selected from the group consisting of extra cellular matrix of chondrocytes (ECM), a hormone, an antiviral agent, an anti-inflammatory agent, an analgetic compound, and an antibacterial agent.

4. The composition of claim 1 wherein said microcapsule is contained in a hydrogel wafer.

5. The composition of claim 4 wherein said hydrogel wafer comprises a material selected from the group consisting of agar, gelatin, gellan gum and agarose.

6. A method for promoting bone regeneration, comprising administration of the composition of any one of claims 1, 3, 4, and 5 to an individual in need of said treatment.

7. The method of claim 6 wherein said individual is a mammal.

8. The method of claim 7 wherein said mammal is selected from the group consisting of a human, a dog, a cat, and a horse.

9. The method of claim 7 wherein said mammal is a human.

* * * * *